(12) United States Patent
Carter et al.

(10) Patent No.: US 11,045,110 B2
(45) Date of Patent: Jun. 29, 2021

(54) SYSTEM AND METHOD OF CANCELLATION OF SOURCE INDUCED ERRORS

(71) Applicant: St. Jude Medical International Holding S.à r.l., Luxembourg (LU)

(72) Inventors: Darren Carter, Shoreview, MN (US); Ryan Albu, Minneapolis, MN (US)

(73) Assignee: St. Jude Medical International Holding S.à r.l., Luxembourg (LU)

( * ) Notice: Subject to any disclaimer, the term of this patent is extended or adjusted under 35 U.S.C. 154(b) by 0 days.

(21) Appl. No.: 16/075,230

(22) PCT Filed: Feb. 2, 2017

(86) PCT No.: PCT/US2017/016291
§ 371 (c)(1),
(2) Date: Aug. 3, 2018

(87) PCT Pub. No.: WO2017/136599
PCT Pub. Date: Aug. 10, 2017

(65) Prior Publication Data
US 2019/0053737 A1   Feb. 21, 2019

Related U.S. Application Data

(60) Provisional application No. 62/290,818, filed on Feb. 3, 2016.

(51) Int. Cl.
*A61B 5/06* (2006.01)
*A61B 34/20* (2016.01)
*A61B 5/00* (2006.01)

(52) U.S. Cl.
CPC ............ *A61B 5/062* (2013.01); *A61B 5/7203* (2013.01); *A61B 34/20* (2016.02);
(Continued)

(58) Field of Classification Search
CPC ........ A61B 34/20; A61B 5/062; A61B 5/7203
See application file for complete search history.

(56) References Cited

U.S. PATENT DOCUMENTS 6,233,476 B1   5/2001   Strommer et al.
6,498,944 B1   12/2002  Ben-Haim et al.
(Continued)

FOREIGN PATENT DOCUMENTS

CN   104783892 A   7/2015
EP   2896383 A1    7/2015
(Continued)

*Primary Examiner* — Jason M Ip
(74) *Attorney, Agent, or Firm* — Dykema Gossett PLLC

(57) ABSTRACT

A medical device assembly comprises a medical device comprising a shaft having proximal and distal end portions. The device further comprises a sensor at the distal end portion of the shaft that comprises first and second leads extending therefrom to the proximal end portion of the shaft. The device further comprises an electromechanical connector having a plurality of connection points at a first end thereof. First and second of the connection points are electrically connected to the first and second sensor leads, respectively. The connector further comprises an error loop segment electrically coupled to third and fourth connection points. The error loops segment assists in forming a compensation loop that can be used to correct for magnetic noise.

4 Claims, 13 Drawing Sheets

(52) U.S. Cl.
CPC . *A61B 2034/2051* (2016.02); *A61B 2562/222* (2013.01); *A61B 2562/227* (2013.01)

(56) References Cited

U.S. PATENT DOCUMENTS

| | | |
|---|---|---|
| 6,690,963 B2 | 2/2004 | Ben-Haim et al. |
| 6,788,967 B2 | 9/2004 | Ben-Haim et al. |
| 7,197,354 B2 | 3/2007 | Sobe |
| 7,386,339 B2 | 6/2008 | Strommer et al. |
| 7,572,231 B2 | 8/2009 | Pearlman |
| 8,600,480 B2 | 12/2013 | Kariv |
| 9,386,967 B2 | 7/2016 | Miller et al. |
| 2003/0227268 A1 | 12/2003 | Smith |
| 2007/0093928 A1 | 4/2007 | Forster et al. |
| 2010/0168556 A1 | 7/2010 | Shen et al. |
| 2013/0085402 A1 | 4/2013 | Callahan et al. |
| 2014/0002063 A1 | 1/2014 | Ashe |
| 2014/0039302 A1 | 2/2014 | Miller et al. |
| 2015/0201864 A1 | 7/2015 | Govari et al. |
| 2015/0374254 A1 | 12/2015 | Sobe |
| 2016/0003775 A1 | 1/2016 | Parramore et al. |

FOREIGN PATENT DOCUMENTS

| | | |
|---|---|---|
| JP | 2010-017549 A | 1/2010 |
| JP | 2013-020969 A | 1/2013 |
| JP | 2015-134166 A | 7/2015 |

SYSTEM AND METHOD OF CANCELLATION OF SOURCE INDUCED ERRORS

BACKGROUND OF THE INVENTION a. Field of the Invention

This disclosure relates to a system and method for performing one or more diagnostic and/or therapeutic medical procedures, the system comprising, in part, a magnetic field-based medical positioning system. More particularly, this disclosure relates to various components of the system for performing one or more diagnostic and/or therapeutic medical procedures, wherein the components are configured for use in a magnetic field environment created by the magnetic field-based medical positioning system.

b. Background Art

A number of different types of medical positioning systems may be used to aid in the performance of various medical diagnostic and therapeutic procedures relating to different parts of the human anatomy, such as, for example, the heart. Among other things, and generally speaking, these systems may provide the ability to determine the position and orientation (P&O) of one or more medical devices disposed within the body of the patient, such as, for example, catheters and sheaths, for visualization and navigation purposes.

One such type of medical positioning system is a magnetic field-based medical positioning system. Magnetic field-based systems generally include one or more magnetic field generators attached to or placed near the patient bed or another component in the operating environment. The field generators are configured to provide controlled, low-strength AC magnetic fields in an area of interest (i.e., an anatomical region) that are used to determine and track the P&O of one or more magnetic sensors disposed in or on a medical device disposed within the area of interest. More particularly, each magnetic sensor, which may comprise a magnetic coil, is configured to detect and generate a respective signal indicative of one or more characteristics of the magnetic field(s). The medical positioning system then processes the generated signals to produce one or more P&O readings associated with the sensors (and thus the medical device). The P&O of the medical device can thereafter be tracked relative to the magnetic field(s).

As briefly described above, medical devices that may be used with such medical positioning systems include elongate medical devices such as catheters and sheaths. These medical devices generally comprise an elongate shaft having a proximal end portion, a distal end portion, and one or more sensors mounted in or on the shaft at or near the distal end portion thereof. As also briefly described above, the sensors of the medical device may comprise magnetic sensors in the form of coils that are configured to allow the system to determine the P&O of the sensor, and therefore by extension, the medical device. More particularly, each sensor may comprise a loop of wire wound a predetermined number of times around a small diameter core to form a coil having a size that is suitable for packaging within the shaft of the medical device, and for generating a current when placed in a magnetic field that is used by the system to determine the P&O of the sensor.

The foregoing discussion is intended only to illustrate the present field and should not be taken as a disavowal of claim scope.

BRIEF SUMMARY OF THE INVENTION

In various embodiments, the present invention is generally directed to a medical device assembly configured for use in a magnetic field environment.

In one embodiment, a medical device assembly for use in a magnetic field environment can comprise an elongate shaft having a proximal end portion and a distal end portion, a position sensor disposed along said distal end portion of said shaft and electrically coupled to a twisted pair. The twisted pair can comprise a first lead and a second lead and extend from the position sensor to said proximal end portion of said shaft. The medical device assembly can further comprise a device connector having a first end, a second end, and a plurality of connection points disposed at said first end. A first lead pin and a second lead pin of said plurality of connection points can be electrically coupled to said first and second leads, respectively, said connector can further comprise an error loop segment electrically connecting a first device compensation pin with a second device compensation pin of said plurality of connection points. The first and second device compensation connection points can be configured to electrically connect, respectively, with complementary first and second cable compensation connection points of a complementary cable connector configured to be mated with said second end of said device connector to form a compensation loop.

In another embodiment, a junction box can be configured for use with a medical device in a magnetic field environment. The junction box can comprise a sensor amplifier, a compensation amplifier, and a subtractor. The sensor amplifier can be configured to receive a sensor signal and output an amplified sensor signal. The compensation amplifier can be configured to receive a compensation signal and to output an amplified compensation signal. The subtractor can be electrically coupled to the sensor amplifier and the compensation amplifier and can be configured to derive and output a compensated signal from the amplified sensor signal and the amplified compensation signal.

In another embodiment, a system for outputting a compensated sensor signal of a medical device can comprise the medical device comprising a sensor coupled to a sensor twisted pair and configured to transmit a first sensor signal. The sensor twisted pair can extend through a portion of the medical device and can be coupled to a device connector. The device connector can further comprise a first device compensation pin, a second device compensation pin, and an error loop segment. The error loop segment can be electrically coupled to the first compensation pin and the second compensation pin. A cable can comprise a first cable connector, a second cable connector, a cable twisted pair, and a compensation twisted pair. The cable twisted pair and the compensation twisted pair can be coupled to the first cable connector and to the second cable connector. The first cable connector can be configured to couple to the device connector, and the second cable connector can be configured to couple to a junction box. The junction box can comprise a sensor amplifier, a compensation amplifier, and a subtractor. The sensor amplifier can be configured to receive the first sensor signal transmitted by the magnetic sensor and output an amplified sensor signal to the subtractor. The compensation amplifier can be configured to receive a compensation signal from the compensation twisted pair and output an amplified compensation signal to the subtractor, and the subtractor can be configured to derive and output a compensated signal from the amplified sensor signal and the amplified compensation signal.

The foregoing and other aspects, features, details, utilities, and advantages of the present invention will be apparent from reading the following description and claims, and from reviewing the accompanying drawings.

DETAILED DESCRIPTION OF EMBODIMENTS OF THE INVENTION

Various embodiments are described herein of various apparatus and/or systems. Numerous specific details are set forth to provide a thorough understanding of the overall structure, function, manufacture, and/or use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," "an exemplary embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," "in an exemplary embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
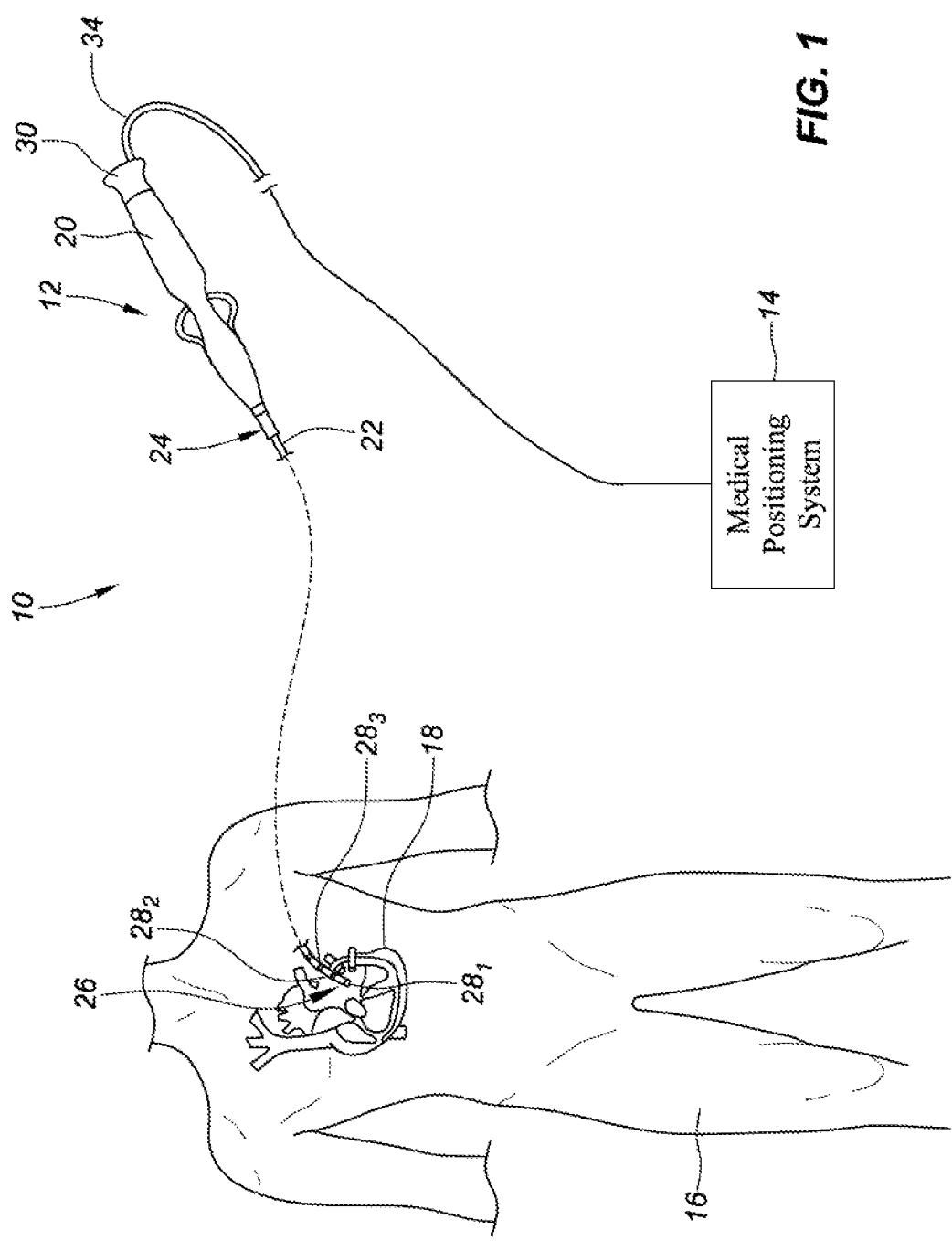
FIG. 1 is a diagrammatic view of a system for performing one or more diagnostic or therapeutic procedures, wherein the system comprises a magnetic field-based medical positioning system, in accordance with the present teachings.

Referring now to the drawings wherein like reference numerals are used to identify identical or similar components in the various views, FIG. 1 illustrates one embodiment of a system 10 for performing one or more diagnostic and/or therapeutic medical procedures relating to different parts of the human anatomy, such as, for example, the heart. For purposes of clarity and illustration, the description set forth below will be with respect to a system used for cardiac-related applications only. It should be understood, however, that the present disclosure may be implemented and find use in connection with any number of other anatomical-related applications. Accordingly, the present disclosure is not intended to be limited to cardiac-related applications.

In one embodiment, and with reference to FIG. 1, the system 10 comprises a medical device 12 and a medical positioning system 14. The medical device 12 may comprise an elongate medical device such as, for example, catheter or a sheath. For purposes of illustration and clarity, the description below will be limited to an embodiment wherein the medical device 12 comprises a catheter (catheter 12). It will be appreciated, however, that the present disclosure is not meant to be limited to such an embodiment, but rather in other embodiments, the medical device may comprise other elongate medical devices, such as, for example and without limitation, sheaths, introducers and the like.

With continued reference to FIG. 1, the catheter 12 is configured to be inserted into a patient's body 16, and more particularly, into the patient's heart 18. The catheter 12 may include a handle 20, a shaft 22 having a proximal end portion 24 and a distal end portion 26, and one or more sensors 28 mounted in or on the shaft 22 of the catheter 12. As used herein, "sensor 28" or "sensors 28" may refer to one or more sensors $28_1$, $28_2$, ... $28_N$, as appropriate and as generally illustrated. In one embodiment, the sensors 28 are disposed at the distal end portion 26 of the shaft 22. The catheter 12 may further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads. In one embodiment, the catheter 12 further comprises an electromechanical connector 30 configured to allow the catheter 12, and the sensors 28 thereof, in particular, to be coupled with other components of the system 10, such as, for example, the medical positioning system 14.

The handle 20, which is disposed at the proximal end portion 24 of the shaft 22, provides a location for the clinician to hold the catheter 12 and may further provide means for steering or guiding the shaft 22 within the body 16 of a patient. For example, the handle 20 may include means to manipulate one or more steering wires extending through the catheter 12 to the distal end portion 26 of the shaft 22 to steer the shaft 22. The handle 20 is conventional in the art and it will be understood that the construction of the handle 20 may vary. In another embodiment, the catheter 12 may be robotically driven or controlled. Accordingly, in such an embodiment, rather than a clinician manipulating a handle to steer or guide the catheter 12, and the shaft 22 thereof, in particular, a robot is used to manipulate the catheter 12.

The shaft 22 is an elongate, tubular, flexible member configured for movement within the body 16. The shaft 22 supports, for example and without limitation, sensors and/or electrodes mounted thereon, such as, for example, the sensors 28, associated conductors, and possibly additional electronics used for signal processing and conditioning. The shaft 22 may also permit transport, delivery, and/or removal of fluids (including irrigation fluids, cryogenic ablation fluids, and bodily fluids), medicines, and/or surgical tools or instruments. The shaft 22 may be made from conventional materials such as polyurethane, and defines one or more lumens configured to house and/or transport electrical conductors, fluids, or surgical tools. The shaft 22 may be introduced into a blood vessel or other structure within the body 16 through a conventional introducer. The shaft 22 may then be steered or guided through the body 16 to a desired location, such as the heart 18, using means well known in the art.

The sensors 28 mounted in or on the shaft 22 of the catheter 12 may be provided for a variety of diagnostic and therapeutic purposes including, for example and without limitation, electrophysiological studies, pacing, cardiac mapping, and ablation. In one embodiment, one or more of the sensors 28 are provided to perform a location or position sensing function. More particularly, and as will be described in greater detail below, one or more of the sensors 28 are configured to be a position sensor that provides information relating to the location (position and orientation, or "P&O") of the catheter 12, and the distal end portion 26 of the shaft 22 thereof, in particular, at certain points in time. Accordingly, in such an embodiment, as the catheter 12 is moved along a surface of a structure of interest of the heart 18 and/or about the interior of the structure, the sensor(s) 28 can be used to collect location data points that correspond to the surface of, and/or other locations within, the structure of interest. These location data points can then be used for a number of purposes such as, for example and without limitation, the construction of surface models of the structure of interest. For purposes of clarity and illustration, the description below will be with respect to an embodiment wherein a single sensor 28 of the catheter 12 comprises a position sensor. It will be appreciated, however, that in other embodiments, which remain within the spirit and scope of the present disclosure, the catheter 12 may comprise more than one position sensor as well as other sensors or electrodes configured to perform other diagnostic and/or therapeutic functions. As will be described in greater detail below, the sensor 28 comprises a pair of leads $32_1$, $32_2$ extending from a sensing element thereof (e.g., a coil) that are configured to electrically couple the sensor 28 to other components of the system 10, such as, for example, the medical positioning system 14.

Figure 2:
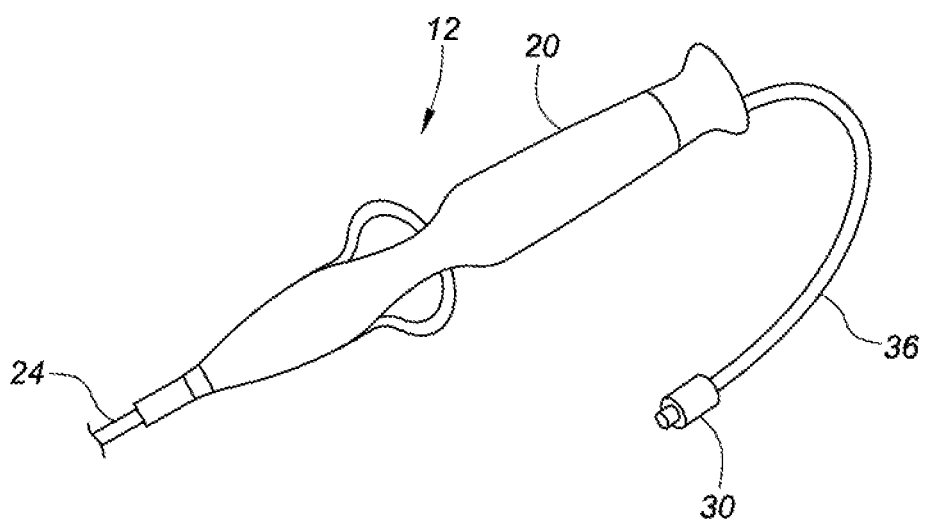
FIG. 2 is a diagrammatic view of a portion of an elongate medical device, such as, for example, a catheter, configured for use in the system illustrated in FIG. 1.

As will be described in greater detail below, the electromechanical connector 30 provides electrical and mechanical connection(s) for, among other things, the leads $32_1$, $32_2$ of the sensor 28 of the catheter 12, as well as wires or cables, such as, for example, a cable 34 extending between the catheter 12 and other components of the system 10 (e.g., the medical positioning system 14, an ablation generator, an electrophysiology recording system, a junction box, a stimulation system, a tissue contact sensing system, etc.). In one embodiment, and as illustrated in FIG. 1, the connector 30 is disposed within the handle 20 of the catheter 12. In another embodiment, rather than being disposed within or as part of the handle 20, the connector 30 is disposed apart from the handle 20. For example, and as illustrated in FIG. 2, the connector 30 may be disposed at the end of a pigtail 36 extending from the handle 20 of the medical device 12.

Figure 3A:
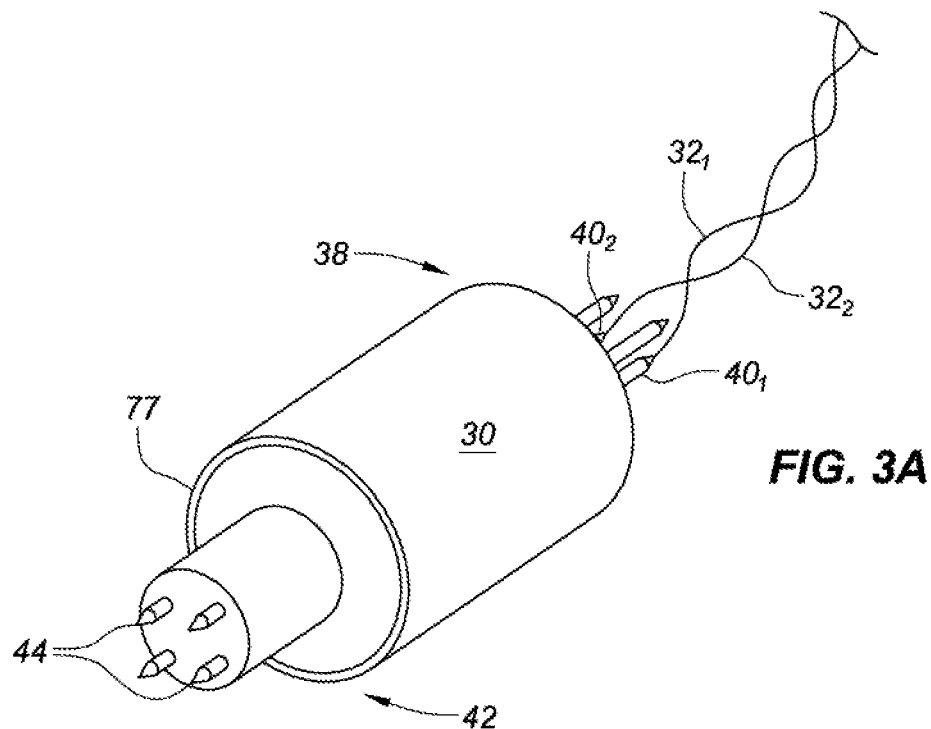
FIGS. 3a and 3b are isometric views of alternate embodiments of an electromechanical connector of the medical device illustrated in FIG. 2.
Figure 3B:
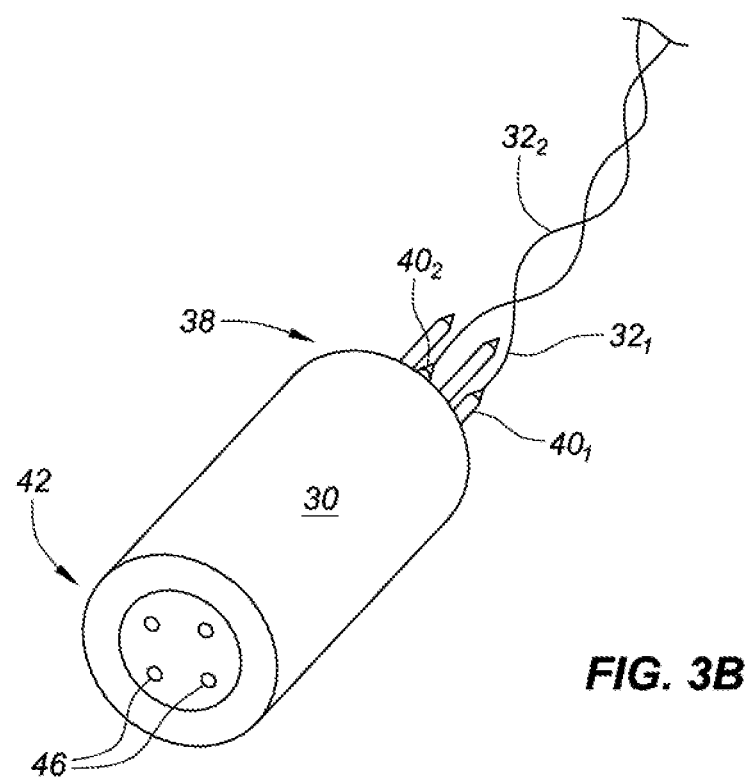

Regardless of where the connector 30 is located, in an embodiment such as that illustrated in FIGS. 3a and 3b, a first end 38 of the connector 30 has a plurality of connection points 40, and each lead of the pair of leads $32_1$, $32_2$ of the sensor 28 is electrically and mechanically connected or coupled to a respective one of the connection points 40. As used herein, "connection point 40" or "connection points 40" may refer to one or more connection points $40_1$, $40_2$, ... $40_N$, as appropriate and as generally illustrated. In one embodiment, each of the connection points can comprise a pin. A second end 42 of the connector 30 opposite the first end 38 is configured to provide an interface between the catheter 12, and the sensor 28 thereof, in particular, and other components of the system 10, such as, for example, the medical positioning system 14 or a junction box. For example, in one embodiment such as that illustrated in FIG. 3a, the second end 42 of the connector 30 may take the form of a male plug connector having a plurality of connection points 44 that are electrically coupled to, or that comprise, the connection points 40 disposed at the first end 38 of the connector 30 (e.g., the connection points 40 may extend through the first and second ends 38, 42 of the connector 30). In such an embodiment, the second end 42 of the connector 30 is configured to be mated with a complementary female receptacle connector having a plurality of socket contacts configured to receive the connection points 44 of the connector 30. Alternatively, as illustrated in FIG. 3b, the second end 42 of the connector 30 may take the form of a female receptacle connector having a plurality of sockets 46 configured to receive a corresponding number of connection points from a complementary male plug connector of a cable.

Accordingly, regardless of the particular form the connector 30 takes, it is configured to allow for the electrical connection of the catheter 12, and the sensor 28 thereof, to one or more components of the system 10, such as, for example, the medical positioning system 14.

One drawback to the use of these types of medical devices in conjunction with a magnetic field-based medical positioning system is that any loops of wire that are considered separate or apart from the sensor can act as a magnetic pickup when subjected to magnetic fields. This may result in noise or interference being added to the signal generated by the sensor, thereby potentially adversely impacting the accuracy of the P&O determination based thereon (i.e., causing an error in the P&O of the sensor determined based on the signal generated by the sensor). For example, a wire that is wrapped numerous times around a core to form a coil may have two ends or leads extending from the coil. These leads are routed from the coil down the shaft of the medical device where they are terminated in an electrical connector that allows for the sensor to be electrically coupled to other components of, for example, the medical positioning system or components that are intermediate thereto (e.g., amplifiers, processors, etc.). However, when arranged within the shaft of the medical device, these two leads may serve to form a loop of wire that may generate a current when subjected or exposed to a magnetic field. As described above, this may result in the addition of noise or interference to the current signal being transmitted from the sensor.

In the catheter itself one conventional technique used to address the above-described problem is to arrange the two leads of a sensor in a twisted pair pattern along the lengths of the leads from the sensor to the termination point. Such an arrangement is known to prevent, or at least substantially minimize, magnetic pickup in the wires. Accordingly, by preventing magnetic pickup along the length of the shaft of the medical device, interference or noise that may adversely impact the signals generated and transmitted by the sensor is prevented or at least substantially minimized. However, while this technique has been useful in limiting interference generated along the length of the shaft of the medical device, it does not completely solve the problem with respect to other areas or locations of the medical device or within the system of which it is a part. In one embodiment, the twisted pair can comprise a pair of twisted cables. In another embodiment, the twisted pair can comprise printed conductors. In yet other embodiments, the twisted pair can comprise other methods known to one of ordinary skill in the art. These embodiments are further described in U.S. application Ser. No. 14/790,541, filed 2 Jul. 2015, which is hereby incorporated by reference as though fully set forth herein.

As described above, the two leads of the sensor are terminated at an electrical connector that may be disposed at or near the proximal end portion of the shaft (e.g., within or near the handle of the device located proximate the proximal end portion of the shaft). Because the handle portion of the medical device, and therefore, the electrical connector to which the leads are coupled, is disposed in close proximity to the patient during a procedure, the electrical connector and cable may be subjected or exposed to the magnetic field(s) applied by the medical positioning system. As a result, the electrical connector can cable can act as a magnetic pickup, and therefore, a current may be induced by the magnetic field(s). As described above, such a generated current may result in noise or interference to the signal generated and transmitted by the sensor, which may introduce not insignificant error in the sensor location determined therefrom.

Figure 4:
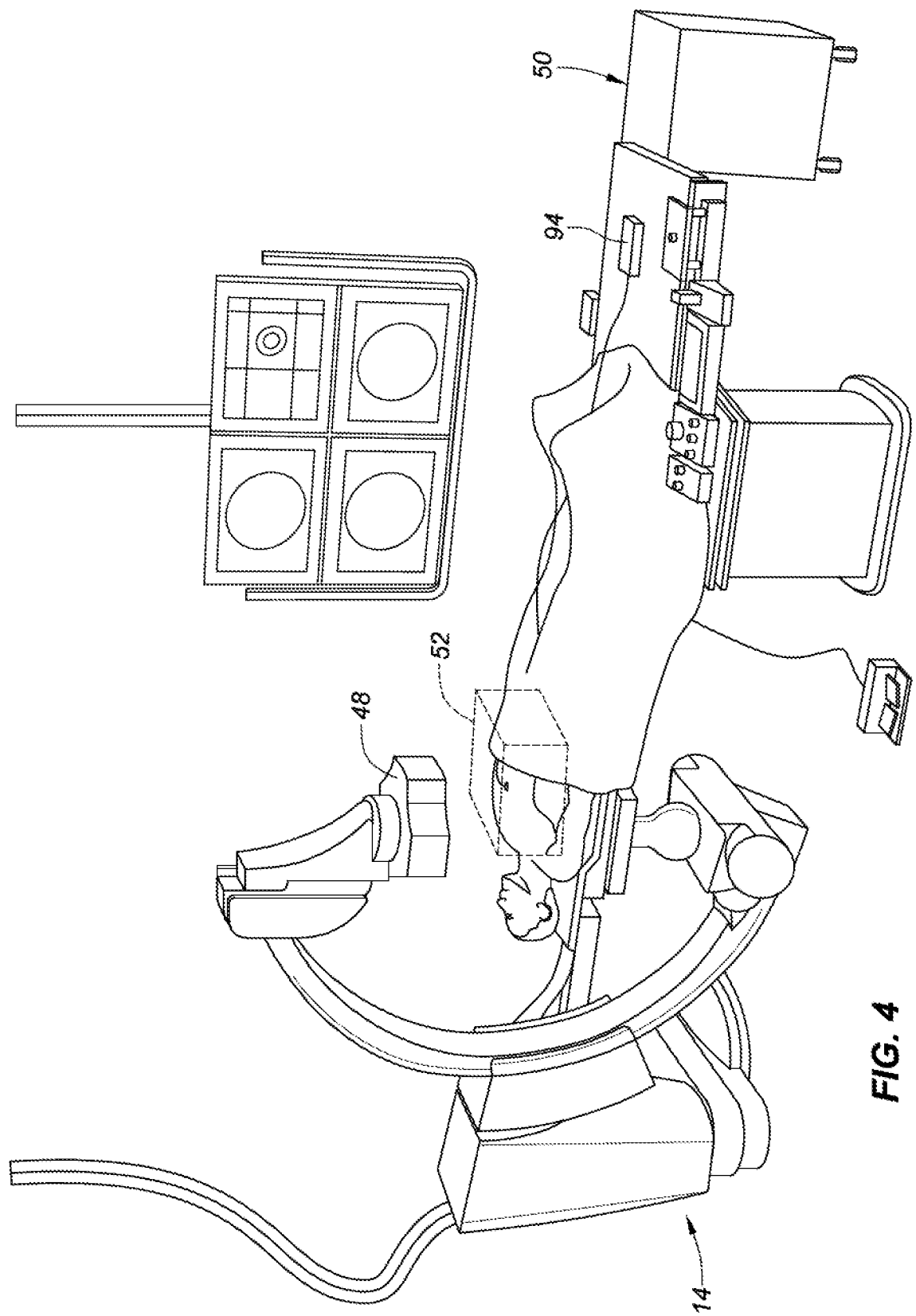
FIG. 4 is a diagrammatic view of a magnetic field-based medical positioning system configured for use in the system illustrated in FIG. 1.

With reference to FIGS. 1 and 4, the medical positioning system 14 will now be described. The medical positioning system 14 is provided for determining the P&O of the sensor 28 of the catheter 12, and thus, the P&O of the catheter 12. In one embodiment, the medical positioning system 14 may comprise a magnetic field-based system such as, for example, the Carto™ System available from Biosense Webster, and as generally shown with reference to one or more of U.S. Pat. Nos. 6,498,944; 6,788,967; and 6,690,963, the entire disclosures of which are incorporated herein by reference, or the MediGuide™ system from MediGuide Ltd. (now owned by St. Jude Medical, Inc.), and as generally shown with reference to one or more of U.S. Pat. Nos. 6,233,476; 7,197,354; and 7,386,339, the entire disclosures of which are incorporated herein by reference. Alternatively, the medical positioning system 14 may comprise a combination magnetic field-based system and electric field-based system such as, for example and without limitation, the Carto 3™ System also available from Biosense Webster.

In one embodiment, and in general terms, the medical positioning system 14 comprises, at least in part, a magnetic transmitter assembly (MTA) 48 and a magnetic processing core 50 for making P&O determinations. The MTA 48 is configured to generate low-strength magnetic field(s) in and around the patient's chest cavity in a predefined three-dimensional space designated as motion box 52 in FIG. 4. In such an embodiment, and as briefly described above, the catheter 12 includes a position sensor 28 comprising a magnetic sensor configured to detect one or more characteristics of the low-strength magnetic field(s) applied by the MTA 48 when the sensor 28 is disposed within the motion box 52. The sensor 28, which in an embodiment comprises a magnetic coil, is electrically connected to the processing core 50 and configured to generate a signal corresponding to the sensed characteristics of the magnetic field(s) that is provided to the magnetic processing core 50. The processing core 50 is responsive to the detected signal and is configured to calculate a three-dimensional P&O reading for the sensor 28. Thus, the medical positioning system 14 enables real-time tracking of each magnetic sensor 28 of the catheter 12 in three-dimensional space, and therefore, real-time tracking of the catheter 12.

As described above, one drawback to the use of a magnetic field-based medical positioning system in conjunction with elongate medical devices, such as catheters, is that any loops of wire that are separate and distinct from the sensing element (e.g., coil) of the sensor 28 can act as a magnetic pickup when subjected to magnetic fields. As a result, noise or interference may be added to the signals generated by the sensor 28, thereby resulting in not insignificant errors being introduced into P&O determinations based on those signals. For example, and with reference to FIGS. 1-3b, in the instance wherein the sensor 28 comprises a magnetic coil formed by a wire wrapped numerous times around a core, the leads $32_1$, $32_2$ of the sensor 28 are routed from the coil down the shaft 22 of the catheter 12 to the proximal end thereof where they may be terminated in an electromechanical connector, such as, for example, the connector 30. More particularly, the leads $32_1$, $32_2$ may be coupled (e.g., soldered, crimped, etc.) to respective connection points 40 of the connector 30. However, over the length of the shaft 22, the leads $32_1$, $32_2$ may form a loop of wire that may act as a magnetic pickup when subjected or exposed to a magnetic field, thereby causing interference to the signals generated by the sensor 28. To prevent this from occurring, the leads $32_1$, $32_2$ may be arranged in a twisted pair pattern along the lengths thereof from the sensing element of the sensor 28 to a point near the termination point of the leads $32_1$, $32_2$ at the connector 30.

Figure 5:
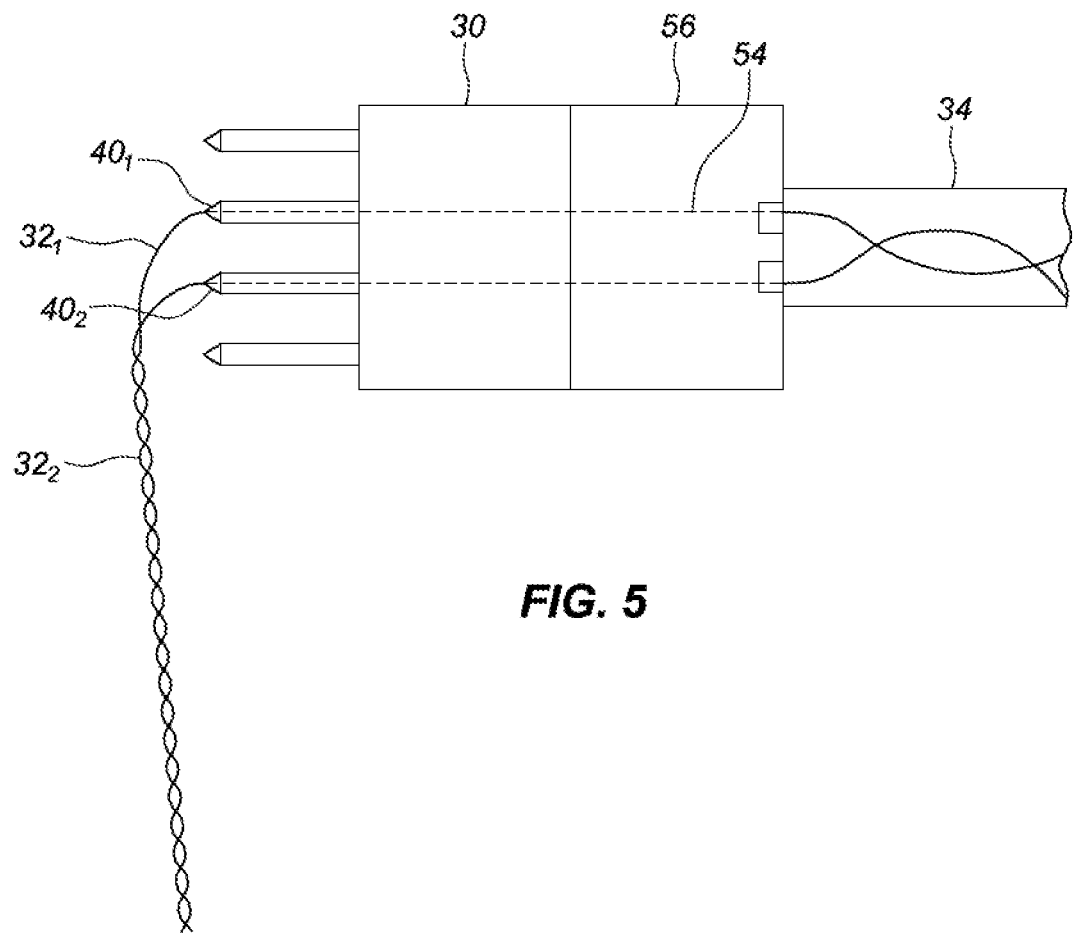
FIG. 5 is a diagrammatic view of a conventional connection arrangement between two electromechanical connectors illustrating a magnetic pickup loop created between the two connectors when the connectors are mated together.

While the twisted pair arrangement of the leads $32_1$, $32_2$ themselves is suitable to prevent the generation of noise within the leads $32_1$, $32_2$ along their length, it does not provide a complete solution to the problem. More particularly, in order to be connected to the connection points 40 of the connector 30, the leads $32_1$, $32_2$ may be untwisted and then connected to respective connection points 40. For example, in the embodiments illustrated in FIGS. 3a and 3b, the leads $32_1$, $32_2$ are untwisted and then coupled or connected to connection points $40_1$, $40_2$, respectively. The combination of the untwisted portion of the leads $32_1$, $32_2$, the length of the connection points 40 (e.g., $40_1$, $40_2$), and the relatively large distance or space between the connection points 40 results in, as illustrated in FIG. 5, the formation of a magnetic loop 54 when the connector 30 is mated with a corresponding electromechanical connector 56 of a cable, such as, for example, the cable 34. Due to the location of the connection between the connector 30 and the connector 56, which is in relatively close proximity to the patient bed, this loop 54 may be subjected or exposed to the magnetic field(s) applied by the MTA 48, and therefore, may generate noise or interference in the signal generated by the sensor 28.

One way to minimize the noise or interference in the signal is to join the connector 30 with a complementary connector (e.g., the connector 56), and form a second magnetic loop 58 that is substantially equal in area and opposite in orientation to the magnetic loop formed by the pair of leads extending from the sensor to the junction box. As such, when the connection between the connector 30 and connector 56 is subjected or exposed to a magnetic field, the currents induced in the two loops will be equal but opposite, thereby resulting in the currents offsetting each other. Thus, interference to the signals generated by the sensor 28 and transmitted through the connectors 30, 56 is prevented or at least substantially minimized. This method is further described in U.S. application Ser. No. 13/563,239, filed 31 Jul. 2012, which is hereby incorporated by reference as though fully set forth herein.

Figure 6:
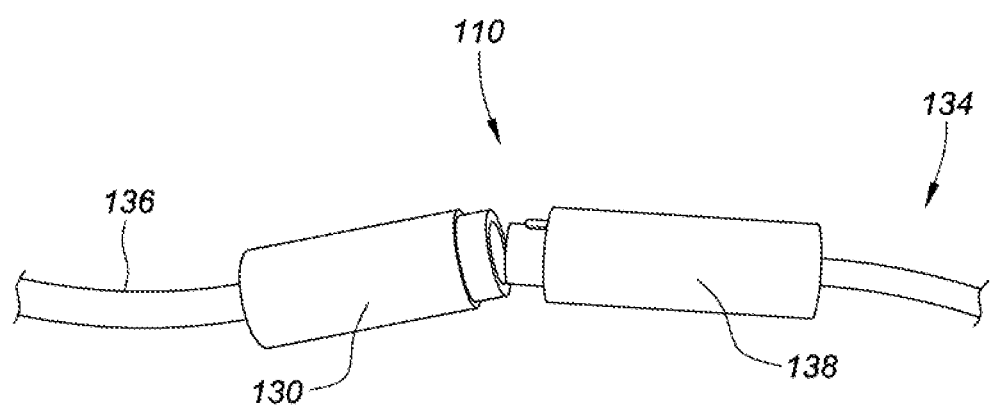
FIG. 6 is an isometric view of one embodiment of a connection arrangement between a medical device and a cable.

FIG. 6 illustrates one embodiment of another method of preventing or minimizing the generation of noise or interference. A system 110 is illustrated showing a cable 134 that can comprise a complementary cable connector 138 that can couple to a catheter connector 130 to prevent, or at least minimize, the generation of noise or interference in the connection arrangement or assembly of the connector 130 to the cable 134. In the illustrated embodiment, the catheter connector 130 can be coupled to a pigtail 136 that can extend from a proximal side of a catheter. In other embodiments, the catheter connector can be coupled to a catheter in other ways as discussed within this disclosure and as would be known to one of ordinary skill in the art. When the catheter connector 130 is mated with the pigtail 136 a second magnetic loop can be formed that can be used as an error measurement loop. The error measurement loop can be created in the catheter connector 130, the complementary cable connector 138, and the cable 134 and can be used to remove some of the noise or interference created in the system.

In addition to including an error measurement loop, in an one embodiment, one or both of the catheter connector 130 or the complementary cable connector 138 may also be shielded. More particularly, a magnetic shield 77 (best shown in FIGS. 3a and 10a) formed of a material with high magnetic permeability may placed over the outer housing of one or both of the connectors. More particularly, a magnetic shield formed of what is commonly known as a "mu metal" (e.g., a nickel-iron alloy) can be placed over both the catheter connector 130 and the complementary cable connector 138. The magnetic shield acts to effectively reduce the strength of the magnetic field to which each of the electrical connectors are exposed.

Figure 7A:
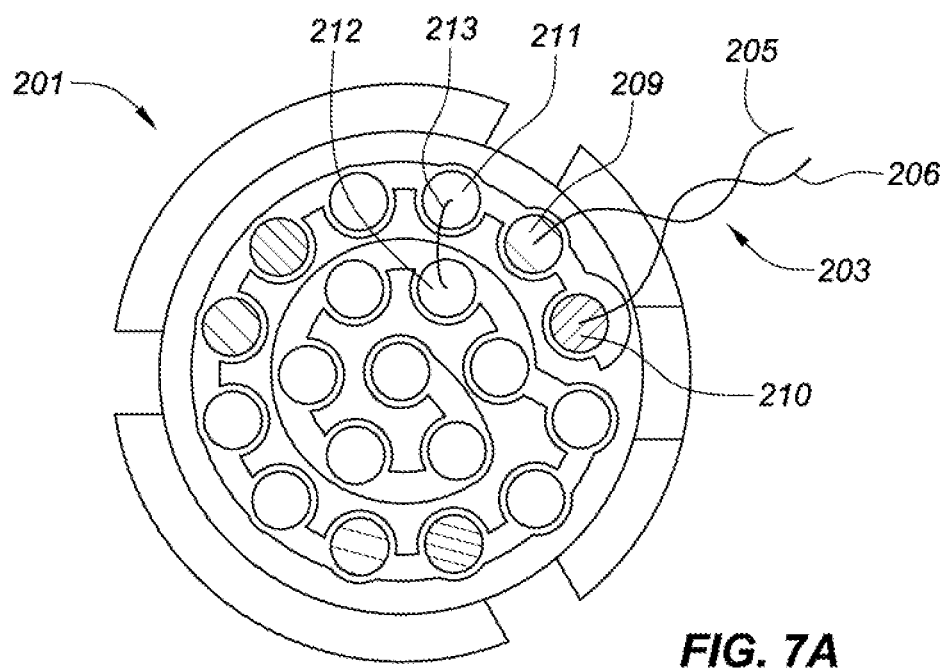
FIGS. 7A and 7B are plan and diagrammatic views of an end of an electromechanical connector, such as, for example, that depicted in FIG. 3a, configured to accommodate at least one sensor lead pair and an error compensation loop segment between respective pairs of connection points of the connector.

FIG. 7A illustrates one embodiment of a connector 201 coupled to a first twisted pair 203 of leads. The connector 201 can comprise a first compensation pin 211, a second compensation pin 212, an error loop segment 213, a first lead pin 209, and a second lead pin 210. The first lead pin 209 can be coupled to a first lead 205 and the second lead pin 210 can be coupled to a second lead 206. The error loop segment 213 can comprise an electrically conductive material and can be coupled to and can extend between the first compensation pin 211 and the second compensation pin 212 and can couple the two connection points to an error measurement loop that can be used to compensate for noise or artifacts created within materials of the connector. In one embodiment, the error loop segment can comprise a jumper cable. The connector 201 can be coupled by the first twisted pair 203 to a catheter comprising a single sensor. In other embodiments, the catheter can comprise multiple sensors and multiple twisted pairs of leads can be coupled to the connector 201. One embodiment of a connector coupled to multiple twisted pairs of leads can be seen in FIG. 7B.

Figure 7B:
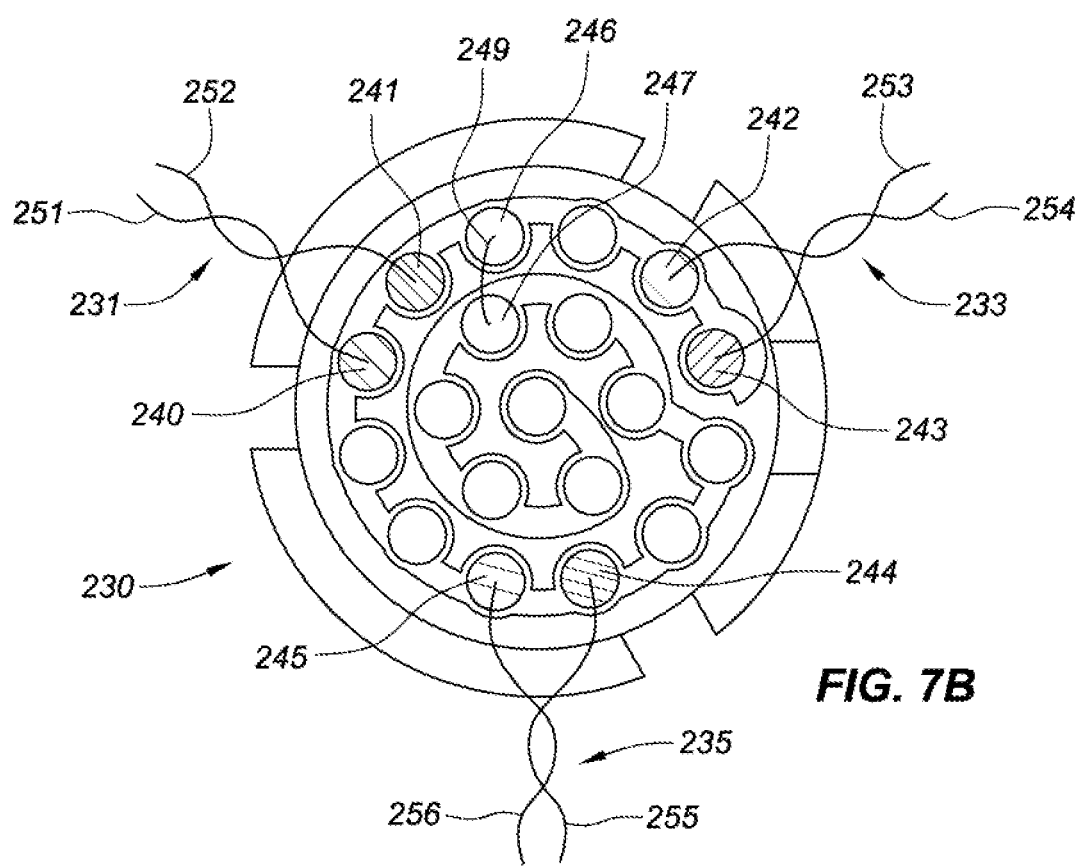

FIG. 7B illustrates another embodiment of a connector 230 coupled to three twisted pairs of leads. The connector 230 can comprise a first compensation pin 246, a second compensation pin 247, an error loop segment 249, a first lead pin 240, a second lead pin 241, a third lead pin 242, a fourth lead pin 243, a fifth lead pin 244, and a sixth lead pin 245. The error loop segment 249 can extend between the first compensation pin 246 and the second compensation pin 247 and can couple the two connection points to an error measurement loop that can be used to compensate for noise or artifacts created within materials of the connector. The connector 230 can be coupled to a first sensor through a first twisted pair 231 that can comprise a first lead 251 and a second lead 252. The connector can be further coupled to a second sensor through a second twisted pair 233 that can comprise a third lead 253 and a fourth lead 254. The connector can be further still coupled to a third sensor through a third twisted pair 235 that can comprise a fifth lead 255 and a sixth lead 256. In other embodiments, the connector can be coupled to varying numbers of sensors or other components of the catheter. In on embodiment, the connector can be further coupled to at least one thermocouple. In another embodiment, the connector can be coupled to one or more electrodes disposed on a distal end of the catheter. The one or more electrodes can be used to deliver ablation energy, sense electrical signals, or be used to determine a location of the electrodes with or without the assistance of the magnetic sensors as discussed herein.

As briefly described above, the system 10 may further comprise a cable (e.g., the cable 134 described above) that may be used to connect the catheter 12 with one or more other components of the system 10. In one embodiment, the catheter 12 and cable 134 may combine to form a medical device assembly, while in another embodiment, the cable 134 may be part of the component of the system 10 to which the catheter 12 is being connected.

Figure 8:
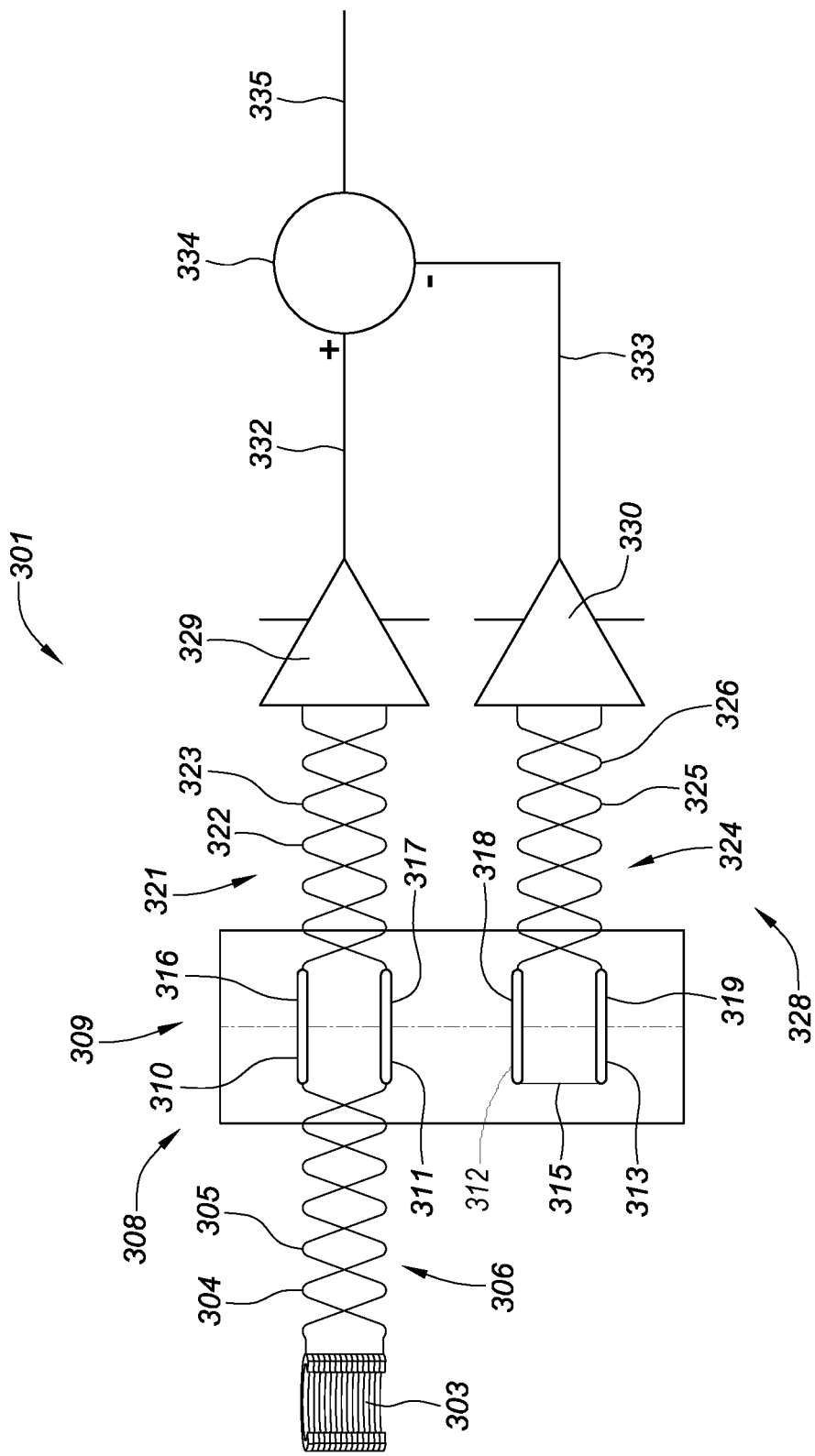
FIG. 8 is a diagrammatic view of an error compensation loop to receive a compensated signal from a magnetic sensor.

FIG. 8 illustrates an embodiment of part of a system to prevent or minimize the generation of noise as described herein. A sensor 303 can be coupled to a sensor twisted pair 306. The sensor 303 can be within a catheter or other medical device as discussed above. The sensor twisted pair 306 can comprise a first sensor lead 304 and a second sensor lead 305 and can extend through the catheter or other medical device to a device connector 308.

The device connector 308 can comprise a first device sensor pin 310, a second device sensor pin 311, a first device compensation pin 312, a second device compensation pin 313, and an error loop segment 315. The first sensor lead 304 can be coupled to the first device sensor pin 310 and the second sensor lead 305 can be coupled to the second device sensor pin 311. The error loop segment 315 can couple the first device compensation pin 312 to the second device compensation pin 313. The device connector 308 can be sized and configured to couple to a first cable connector 309.

The first cable connector 309 can comprise a first cable sensor pin 316, a second cable sensor pin 317, a first cable compensation pin 318, and a second cable compensation pin 319. The first cable sensor pin 316 can be coupled to a first cable lead 322 and the second cable sensor pin 317 can be coupled to a second cable lead 323. The first cable lead 322 and the second cable lead 323 can be twisted together to comprise a cable twisted pair 321. The first cable sensor pin 316 can be configured to be electrically connected to the first device sensor pin 310. The second cable sensor pin 317 can be configured to be electrically connected to the second device sensor pin 311. As a result of the connections, a signal from the sensor 303 can be transmitted through the sensor twisted pair 306, through the device connector 308, the first cable connector 309, and along the cable twisted pair 321. Further, the first cable compensation pin 318 can be coupled to a first compensation lead 325 and the second cable compensation pin 319 can be coupled to a second compensation lead 326. The first compensation lead 325 and the second compensation 326 lead can be twisted together to form a compensation twisted pair 324. The first cable compensation pin 318 can be configured to be electrically connected to the first device compensation pin 312. The second cable compensation pin 319 can be configured to be electrically connected to the second device compensation pin 313.

As a result of the connections described above, noise generated through the device connector 308 and the cable connector 309 can be transmitted through the compensation twisted pair 324 and can be used by the system to remove noise from the signal transmitted through the cable twisted pair 321. The cable twisted pair 321 can be coupled to a sensor amplifier 329 and the compensation twisted pair can be coupled to a compensation amplifier 330. The sensor amplifier 329 can receive a sensor signal from the cable twisted pair 321. An amplified sensor signal 332 can be transmitted from the sensor amplifier 329 to a subtractor 334. The compensation amplifier can receive a compensation signal from the compensation twisted pair 324. An amplified compensation signal 333 can be transmitted from the compensation amplifier 330 to the subtractor 334. The subtractor 334 can subtract the amplified compensation signal 333 from the amplified sensor signal 332 and can then transmit a compensated signal 335. The compensated signal 335 can be transmitted to a medical positioning system or other system or device. The compensated signal 335 can be generated with the use of a compensation loop 328. The compensation loop 328 can comprise the error loop segment 315, the first device compensation pin 312, the second device compensation pin 313, the first cable compensation pin 318, the second cable compensation pin 319, the compensation twisted pair 324, and the compensation amplifier 330. In one embodiment, the sensor amplifier, the compensation amplifier, and the subtractor can be located within a cable as described throughout. The compensated signal can then be output to a junction box or other device. In another embodiment, the sensor amplifier, the compensation amplifier, and the subtractor can be located within a junction box or other element and the cable twisted pair and the compensation twisted pair can be configured to connect to the junction box or other element through a separate connector. In another embodiment, the sensor amplifier, the compensation amplifier, and the subtractor can be present adjacent or within the cable connector.

While FIG. 8 illustrates an embodiment with a single sensor and a single compensation loop. In other embodiments, the system can comprise multiple sensors with a separate twisted pair for each sensor. A subtractor can derive a signal from each of the sensors with a compensation signal from a compensation loop. In yet another embodiment, a system can comprise a plurality of sensors and a plurality of compensation loops. A subtractor can be configured to derive a compensated signal for each of the plurality of sensors by subtracting the signal from a one of the plurality of compensation loops. In yet another embodiment, a system can comprise a plurality of compensation loops and the subtractor can average the signal received from the plurality of compensation loops before deriving a compensated signal for each of the sensor signals. In yet another embodiment, a system can comprise at least one sensor and a plurality of compensation loops and the subtractor can output a separate compensated signal for each of the compensation loops and for each sensor. As an example, if a system comprises a single sensor and two compensation loops, the subtractor can output a first compensated signal using the first compensation loop and a second compensated signal using the second compensation loop. In yet another embodiment, the error loop segment can be removed from the compensation loop and a body compensation twisted pair can extend through the catheter or other medical device and be anchored within an elongate body of the catheter or other medical device. A distal end of the body compensation twisted pair can be shorted together by a conductive segment or welded or brazed together. Any signal generated by compensation loop comprising the body compensation twisted pair can then be used to derive a compensated signal by a subtractor.

Figure 9:
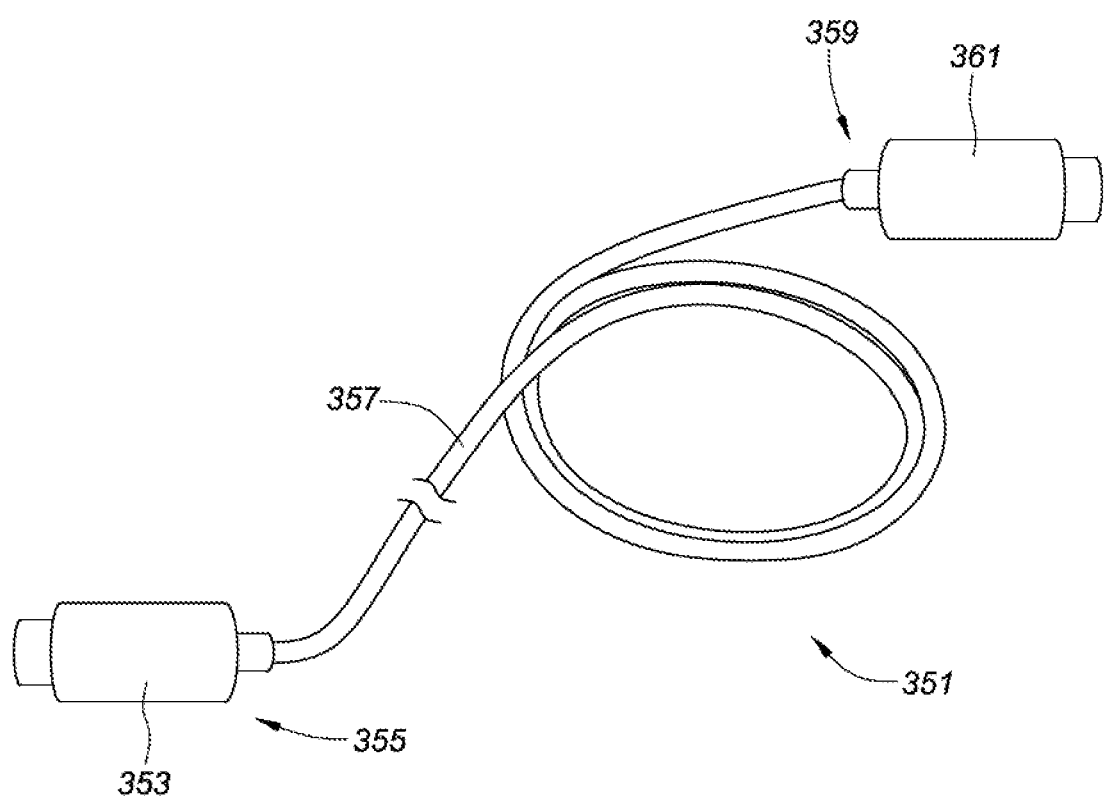
FIG. 9 is an isometric view of an embodiment of an electrical cable configured to electrically connect components of, for example, the system illustrated in FIG. 1.

FIG. 9 illustrates a cable 351 that comprises a first electromechanical connector 353, such as, for example, the connector 56 described above, at a first end 355 thereof, and a second electromechanical connector 361 disposed at a second end 359 thereof. The cable 351 further comprises a plurality of elongate electrical conductors, as described in FIG. 8 above, extending between the first and second connectors 353, 361, and therefore, first and second ends 355, 359. In one embodiment wherein the catheter comprises a single sensor, the cable 351 may comprise two pairs of electrical conductors as described above in relation to FIG. 8. However, in an embodiment wherein the catheter 12 comprises a plurality of sensors 28, the cable 34 may comprise a pair of electrical conductors for each sensor of the catheter, and at least one other pair of electrical conductors for a compensation loop.

As with the sensor leads 32 of the catheter 12, in order to account for the magnetic environment within which the cable 351 may be disposed as a result of its proximity to the magnetic field generated by the medical positioning system 14, each pair of electrical conductors 64 may be arranged in a twisted pair pattern along the length of the cable 34. For purposes of clarity and illustration, the description below will be with respect to an embodiment wherein the catheter 12 comprises a single sensor 28, and as such the cable 34 comprises a single pair of electrical conductors 64 (i.e., electrical conductors $64_1$, $64_2$) for the sensor 28 and a pair of electrical conductors 64 for a compensation loop. As is well known in the art, in addition to the electrical conductors 64 and the connectors 353, 361, the cable 351 may further comprise one or more insulation layers, as well as an outer sheath 357 surrounding the electrical conductors 64.

Figure 10A:
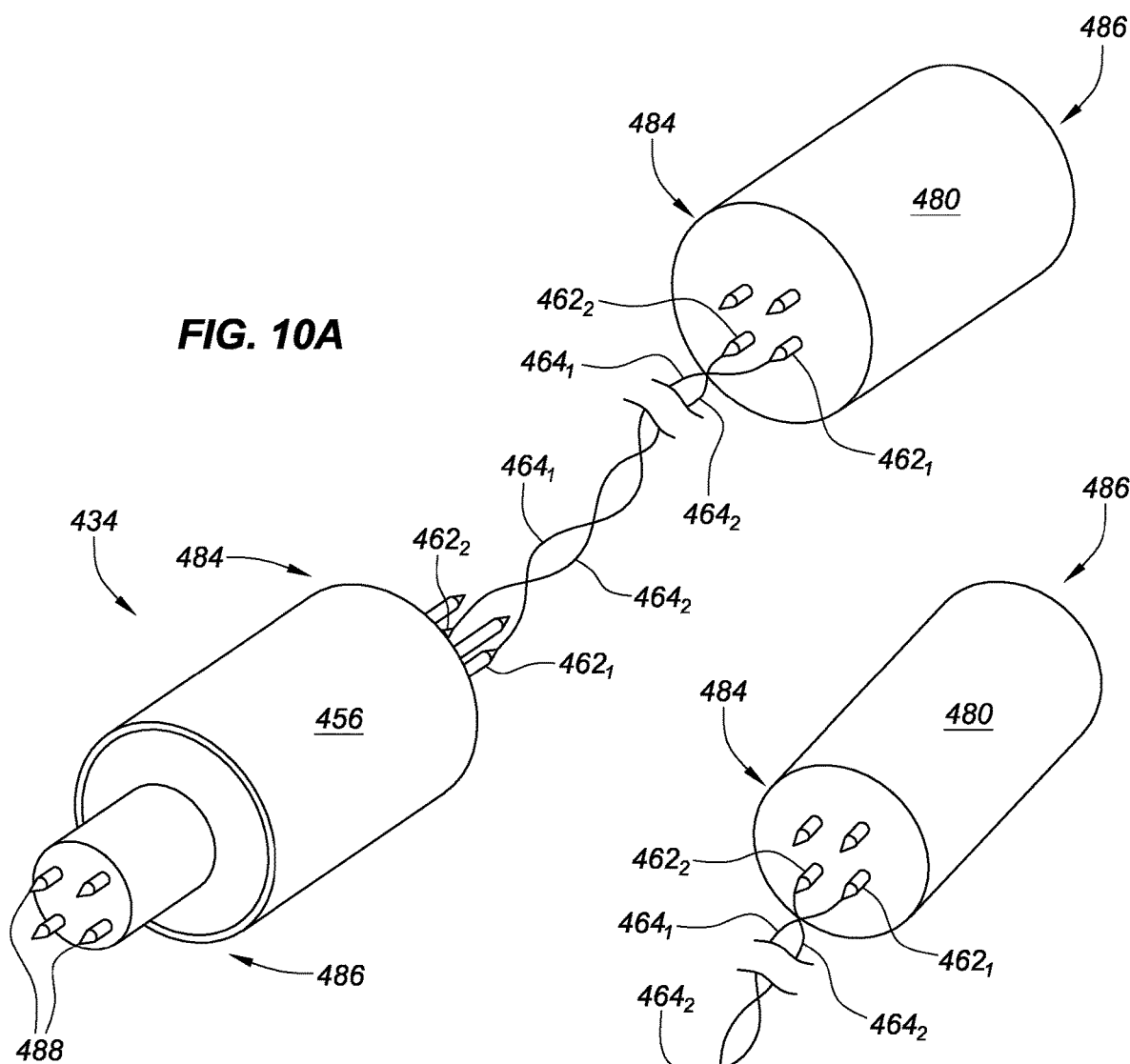
FIGS. 10A and 10B are isometric views of alternate exemplary embodiments of electromechanical connectors of an electrical cable.
Figure 10B:
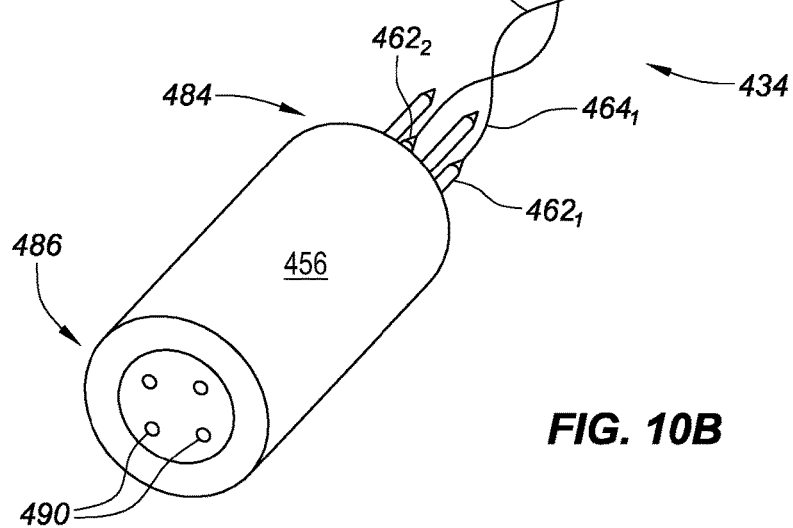

With reference to FIGS. 10a and 10b, and as described above with respect to the connector 30,130 of the catheter 12, each of the connectors 456, 480 comprises a first end 484 and a second end 486. The first end 484 of each connector 456, 480 has a plurality of connection points 462, and each electrical conductor 464 of the cable 434 is electrically and mechanically connected or coupled to a respective one of the connection points 462 of each connector 456, 480 (i.e., one end of each electrical conductor 464 is connected to a respective pin 462 of the connector 456, and the other end of each electrical conductor 464 is connected to a respective pin 462 of the connector 480). The second end 486 of each connector 456, 480 is configured to provide an interface between the cable 434 and the catheter 12, in the case of the cable connector 456, and the cable 434 and another component of the system 10, such as, for example, the medical positioning system 14 or a junction box, in the case of the connector 480.

In one embodiment, such as that illustrated in FIG. 10a, the second end 486 of one or both of the connectors 456, 480 may take the form of a male plug connector having a plurality of connection points 488 that are electrically coupled to, or that comprise, the connection points 462 disposed at the first end 484 of the connector 456, 480 (i.e., the connection points 462 may extend through the first and second ends 484, 486 of the connectors 456, 480). In such an embodiment, the second end(s) 486 of the connector(s) 456, 480 are configured to be mated with a respective complementary female receptacle connector having a plurality of socket contacts configured to receive the connection points 488 of the connector 456, 480. Alternatively, as illustrated in FIG. 10b, the second end 486 of one or both of the connector(s) 456, 480 may take the form of a female receptacle connector having a plurality of sockets 490 configured to receive a corresponding number of connection points from a respective complementary male plug connector.

Accordingly, regardless of the particular form the connectors 456, 480 take, the cable 434 is configured to allow for the electrical connection of the catheter 12, and the sensor(s) 28 thereof, in particular, to one or more components of the system 10, such as, for example, the medical positioning system 14 or, as will be described in greater detail below, a junction box.

As described above, the cable 34 is configured to electrically and mechanically connect the catheter 12, and the sensor 28 thereof, in particular, to one or more other components of the system 10. As also described above, the cable 34 includes an electromechanical connector 80 that is configured be mated with a complementary electromechanical connector of another component of the system 10. One such component is a junction box 94 that, as illustrated in the embodiment depicted in FIG. 4, is disposed between the catheter 12 and, for example, the medical positioning system 14.

The junction box 594 may serve a number of purposes. For example, in one embodiment, such as that illustrated in FIG. 4, the junction box 94 is configured to house at least one amplifier circuit for amplifying the signals generated by the sensors 28. In another embodiment, such as that illustrated in FIG. 11, the junction box 594 may be configured, at least in part, to consolidate a plurality of cables 34 corresponding to a plurality of catheters 12 into a single cable that is then routed to one or more other components of the system 10 (e.g., an amplifier, the medical positioning system 14, an ablation generator, a electrophysiology recording system, a tissue contact sensing system, etc.).

Figure 11:
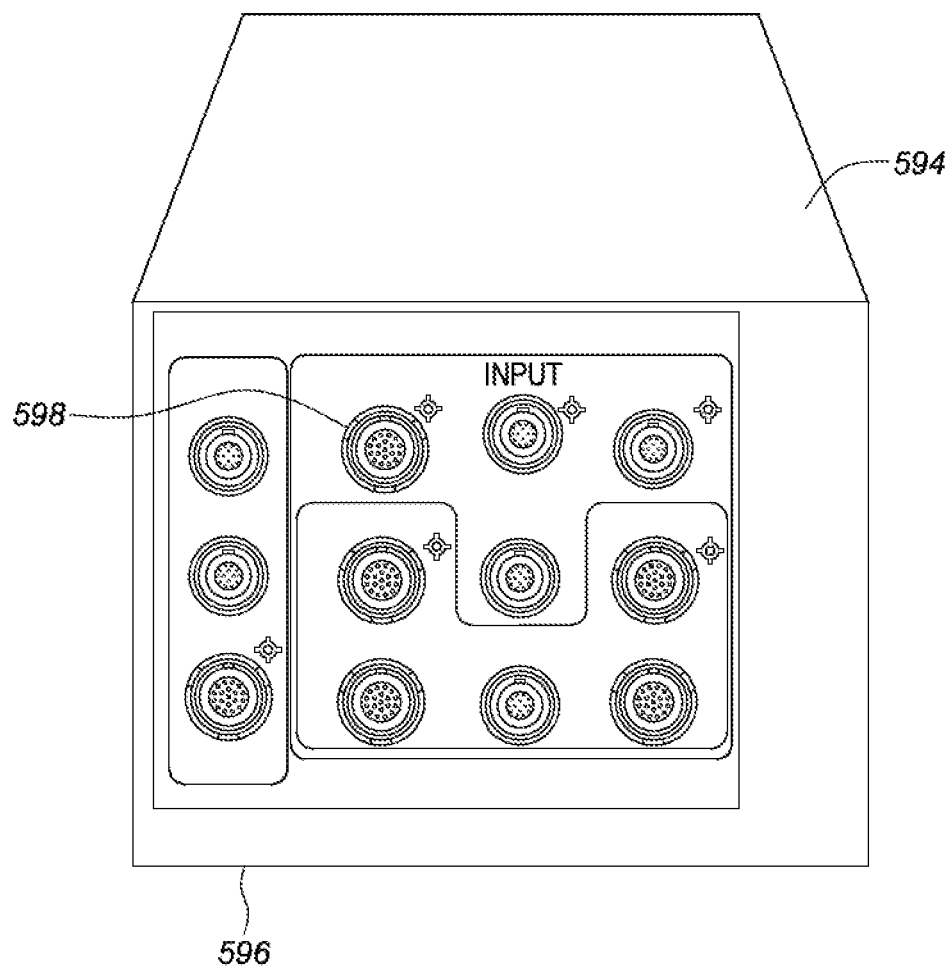
FIG. 11 is a perspective view of a junction box.

In any event, and with reference to FIG. 11, the junction box 594 comprises a housing 596 that is configured to house one or more components. The housing 596 may be constructed of a number of materials, such as, for example, plastic. Due to the proximity of the junction box to magnetic field generated by the medical positioning system 14, the junction box 594 may further include magnetic field shielding. For example, in one embodiment, the junction box 594 may be shielded by a material, such as, for example, mu metal, that is configured as a magnetic shield and acts to effectively eliminate or substantially reduce the strength of the magnetic field to which the components within the housing 594 are exposed.

The junction box 594 can further comprise one or more input ports, each in the form of an electromechanical connector 598, disposed in a wall of the housing 596 that is/are configured to be mated with, for example, one or more respective complementary electromechanical connectors, such as, for example, the connector 80 of the cable 34. In one embodiment a first end of the connector 598 is disposed internal to the housing 596 and has a plurality of connection points. In one embodiment, two or more of the connection points are electrically connected to a header of a circuit board disposed within the housing 596 by respective electrical conductors. A second end of the connector 598 opposite the first end is configured to be mated with, for example, one or more respective complementary electromechanical connectors, such as, for example, the connector 80 of the cable 34, and therefore, to provide an interface between the catheter 12, and the sensor(s) 28 thereof, in particular, and the junction box 594.

For example, in one embodiment, the second end of the connector 598 may take the form of a male plug connector having a plurality of connection points that are electrically coupled to, or that comprise, the connection points disposed at the first end of the connector 598. In such an embodiment, the second end of the connector 598 is configured to be mated with a complementary female receptacle connector of a cable, such as, for example, the connector 80 of the cable 34, having a plurality of socket contacts configured to receive the connection points of the connector 598. Alternatively, the second end of the connector 598 may take the form of a female receptacle connector having a plurality of sockets configured to receive a corresponding number of connection points from a complementary male plug connector of a cable, such as, for example, the connector 80 of the cable 34.

For purposes of clarity and illustration, the description below will be limited to an embodiment wherein the junction box 94 has a single input port connector 598. For the same reasons, the description below will be further limited to an embodiment wherein the connector 598 is configured to accommodate a single-sensor catheter such that the first end of the connector 598 comprises only four connection points. It will be appreciated, however, that in other embodiments, the junction box 594 may comprise any number of input ports or connectors 598, as well as connectors 598 that are configured to accommodate catheters having any number of sensors mounted thereon. Therefore, embodiments wherein the junction box 594 comprises two or more connectors 598, or one or more connectors 598 that are each configured to accommodate a catheter having more than one sensor, remain within the spirit and scope of the present disclosure.

In one embodiment, the connector 598 may also be shielded. More particularly, a magnetic shield (not shown) formed of a material with high magnetic permeability may be placed over the outer housing of the connector 598. More particularly, a magnetic shield formed of, for example, mu metal can be placed over the connector 598. The magnetic shield acts to effectively reduce the strength of the magnetic field to which the electrical connector is exposed.

As described elsewhere above, it will be appreciated that while the description of the output port of the junction box 594 has been primarily with respect to an embodiment wherein the connector is configured to accommodate a single-sensor catheter 12, the present disclosure is not meant to be so limited. Rather, in other embodiments, the junction box 594 may comprise one or more output port connectors, each configured to accommodate one or more single- or multiple-sensor catheters, and such embodiments remain within the spirit and scope of the present disclosure.

Figure 12A:
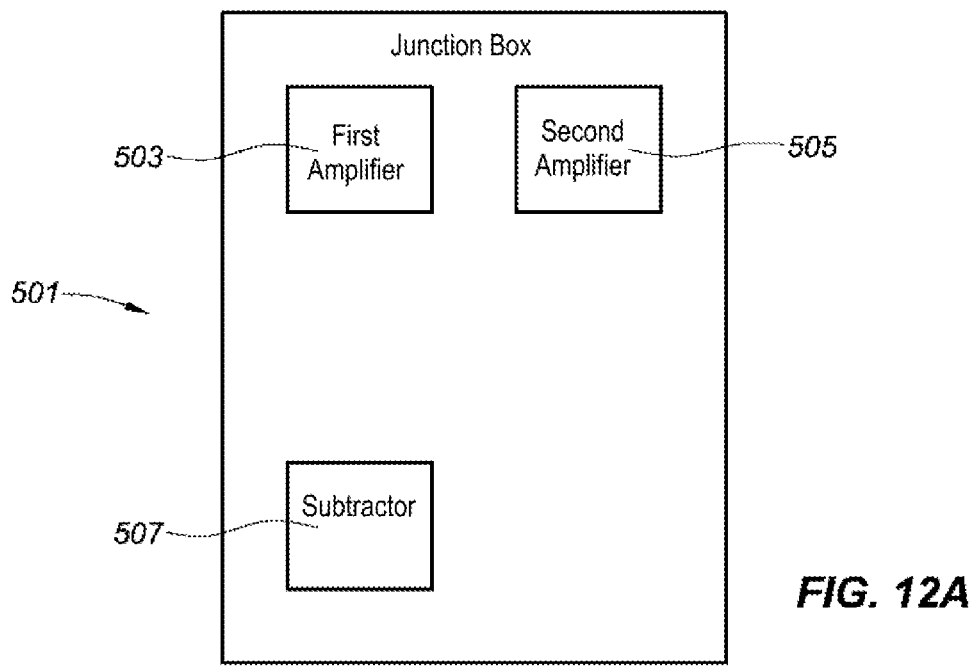
FIGS. 12A and 12B are diagrammatic views of two embodiments of a junction box.
Figure 12B:
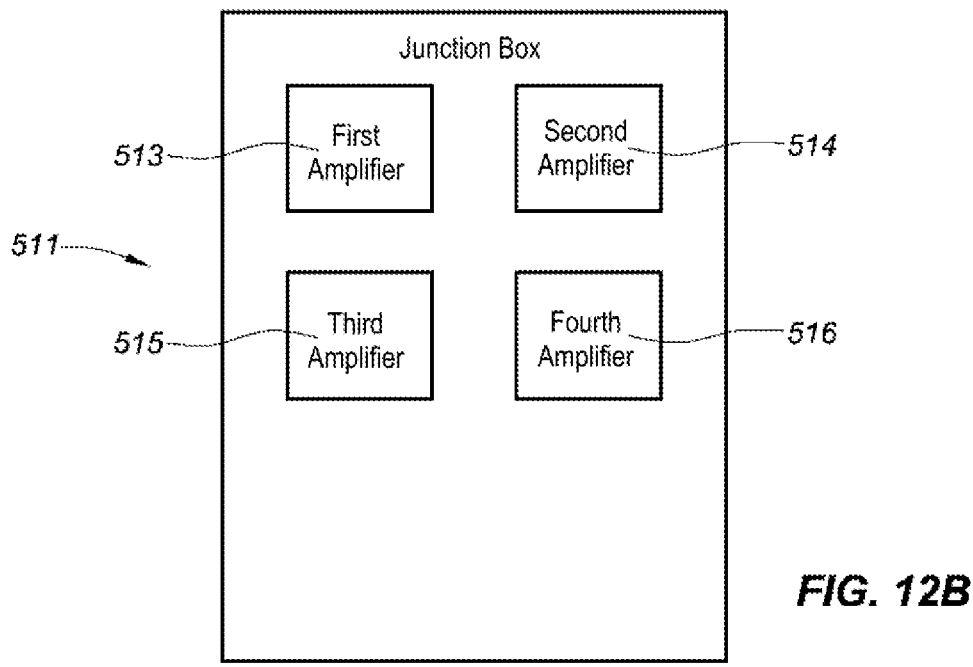

FIGS. 12A and 12B illustrate two embodiments of a junction box according to the disclosure. FIG. 12A illustrates a junction box 501 comprising a first amplifier 503, a second amplifier 505, and a subtractor 507. The junction box 501 can receive a signal from a sensor and a compensation loop. The junction box 501 can then amplify the signals from the sensor and the compensation loop and derive a compensated signal from the amplified signals. The junction box 501 can then output a compensated signal to an external component that can process the compensated signal. FIG. 12B illustrates another embodiment of a junction box 511. The junction box 511 can comprise a first amplifier 513, a second amplifier 514, a third amplifier 515, and a fourth amplifier 516. In one embodiment, the first amplifier 513 can amplify a first sensor signal, the second amplifier 514 can amplify a second sensor signal, the third amplifier 515 can amplify a third sensor signal, and the fourth amplifier 516 can amplify a compensation signal. The junction box 511 can then output the amplified signals to a subtractor or other component that can process the amplified signals to derive at least one compensated signal. In one embodiment, a first compensated signal, a second compensated signal, and a third compensated signal can be derived from a first amplified sensor signal, a second amplified sensor signal, a third amplified sensor signal, and an amplified compensation signal.

Figure 13A:
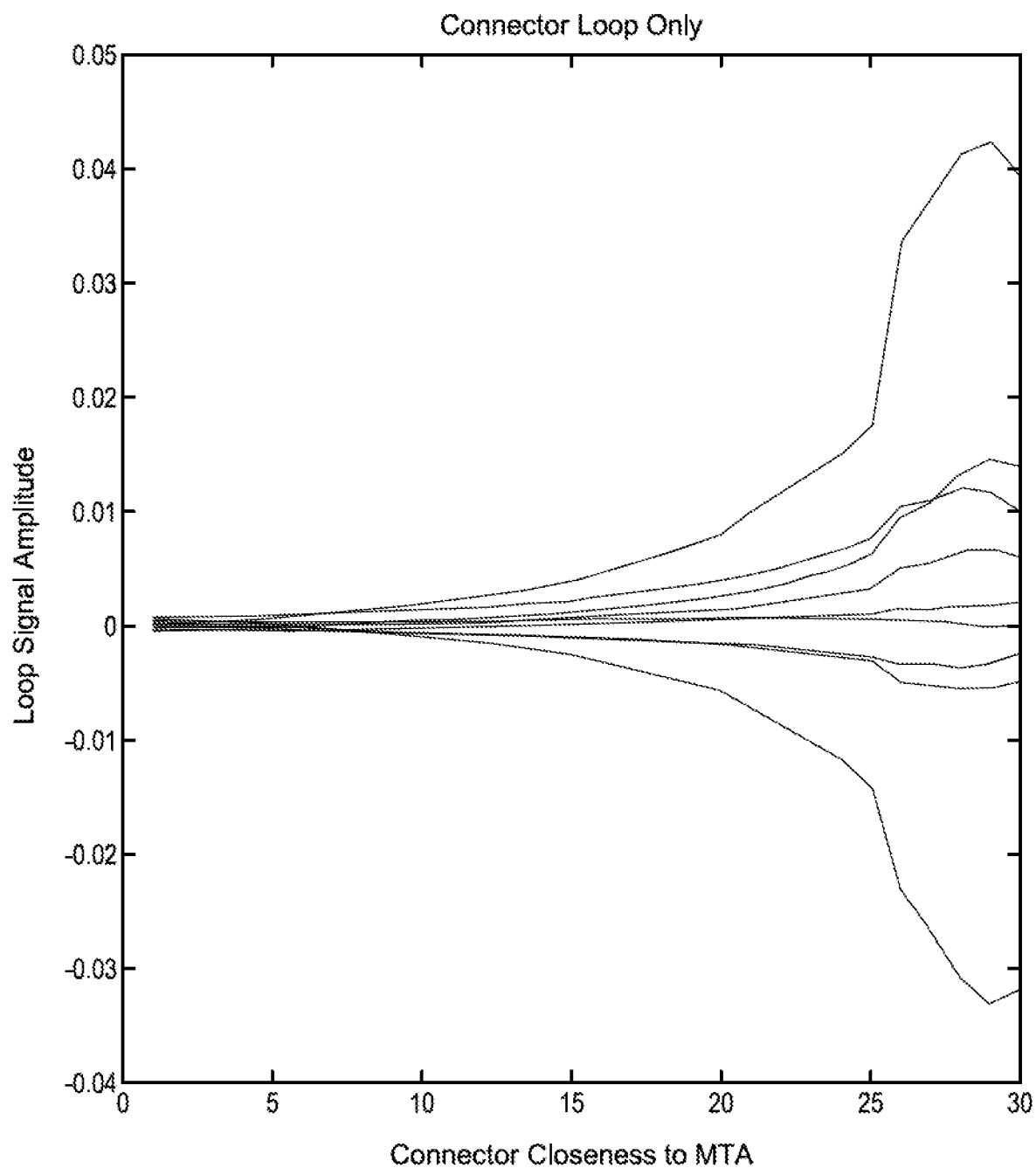
FIG. 13A is a graph illustrating the amount of loop signal amplitude by the closeness of a connector to the MTA.
Figure 13B:
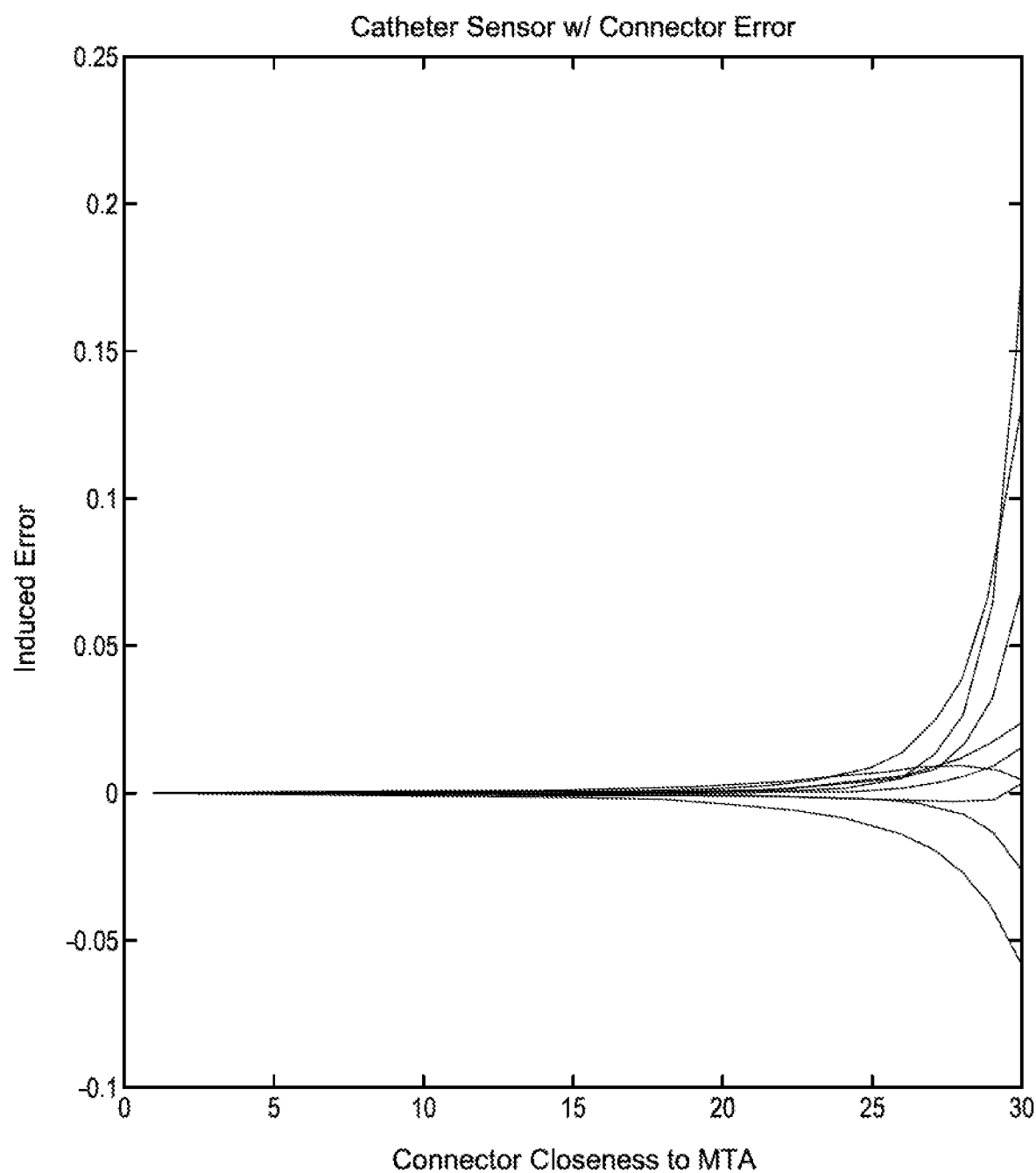
FIG. 13B is a graph illustrating the amount of induced error by the closeness of a connector to the MTA.

FIG. 13A illustrates a loop signal amplitude varying by the closeness of a connector to the MTA. The graph illustrates an embodiment that only includes a connector loop. FIG. 13B illustrates an amount of induced error varying by the closeness of a connector to the MTA. The graph illustrates an embodiment that includes a catheter sensor with connector error.

Although embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A medical device assembly for use in a magnetic field environment, comprising
    an elongate shaft having a proximal end portion and a distal end portion;
    a position sensor disposed along said distal end portion of said shaft and electrically coupled to a twisted pair, wherein said twisted pair comprises a first lead and a second lead and extends from the position sensor to said proximal end portion of said shaft; and
    a device connector having a first end, a second end, and a plurality of connection points disposed at said first end, wherein a first lead pin and a second lead pin of said plurality of connection points are electrically coupled to said first and second leads, respectively, said connector further comprising
        an error loop segment electrically connecting a first device compensation pin with a second device compensation pin of said plurality of connection points, wherein the error loop segment comprises a jumper cable of electrically conductive material extending between the first device compensation pin and the second device compensation pin configured to compensate for noise created within the device connector,
        wherein the jumper cable, first device compensation pin, and the second device compensation pin are electrically separated within the device connector from the first lead, the second lead, the first lead pin, and the second lead pin,
        wherein said first and second device compensation pins are configured to electrically connect, respectively, with complementary first and second cable compensation connection points of a complementary cable connector configured to be mated with said second end of said device connector to form a compensation loop.

2. The medical device assembly of claim 1, wherein said medical device assembly further comprises a handle disposed at said proximal end portion of said shaft, and further wherein said device connector of said medical device is disposed within said handle.

3. The medical device assembly of claim 1, wherein said medical device assembly further comprises a handle disposed at said proximal end portion of said shaft and said first and second leads of said position sensor extend through at least a portion of said handle and form a pigtail extending therefrom, and further wherein said device connector of said medical device is disposed at the end of said pigtail.

4. The medical device assembly of claim 1, further comprising an electrical cable having a first end and a second end, said cable further comprising:
- a first cable lead and a second cable lead arranged in a twisted pair pattern and extending between said first and second ends of said cable;
- a first compensation lead and a second compensation lead arranged in a twisted pair pattern and extending between said first and second ends of said cable; and
- a cable connector disposed at said first end of said cable, said connector of said cable comprising
  - a first end, a second end, and a plurality of connection points disposed at said first end, wherein said first and second cable leads are electrically connected to a first cable sensor pin and a second cable sensor pin of said plurality of connection points of said connector of said cable and wherein said first and second compensation leads are electrically connected to a first cable compensation pin and a second cable compensation pin of said plurality of connection points of said connector of said cable and wherein the cable connector is configured to electrically couple to the device connector.

* * * * *